US006624316B2

(12) United States Patent
Castañedo Cancio et al.

(10) Patent No.: US 6,624,316 B2
(45) Date of Patent: Sep. 23, 2003

(54) METHOD FOR OBTAINING 2-BROMO-5-(2-BROMO-2-NITROVINYL)-FURAN

(75) Inventors: Nilo R. Castañedo Cancio, Villa Clara (CU); Teófilo Exiquio Gaitan Placeres, Villa Clara (CU)

(73) Assignee: Centro de Bioactivos Quimicos (CU)

( * ) Notice: Subject to any disclaimer, the term of this patent is extended or adjusted under 35 U.S.C. 154(b) by 0 days.

(21) Appl. No.: 10/181,541

(22) PCT Filed: Jan. 18, 2001

(86) PCT No.: PCT/CU01/00001

§ 371 (c)(1),
(2), (4) Date: Nov. 4, 2002

(87) PCT Pub. No.: WO01/53283

PCT Pub. Date: Jul. 26, 2001

(65) Prior Publication Data

US 2003/0130529 A1 Jul. 10, 2003

(30) Foreign Application Priority Data

Jan. 18, 2000 (CU) .................................. 8/2000

(51) Int. Cl.$^7$ ...................... C07D 307/52; C07D 307/34
(52) U.S. Cl. ........................ 549/491; 549/497; 549/502; 549/504; 549/505
(58) Field of Search ................ 549/491, 497, 549/502, 504, 505

(56) References Cited

FOREIGN PATENT DOCUMENTS

EP          0678516 A1    10/1995

OTHER PUBLICATIONS

"Synthesis of Some Furylnitro Olefins with Potential Biological Activity," Nazarova et al., Chemical Abstracts, vol. 78, No. 7 (Feb. 19, 1973), p. 463, 43166m.

*Primary Examiner*—Ba K. Trinh
(74) *Attorney, Agent, or Firm*—Lackenbach Siegel LLP

(57) ABSTRACT

The present invention refers to a new procedure for obtaining and purifying 2-bromo-5-(2-bromo-2-nitrovinyl)-furan in one reaction step starting with 2-nitrovinylfuran, and maintains high indexes of purity and an appropriate yield.

The process involves the direct bromination of 2-nitrovinylfuran using charcoal from the beginning of the reaction, followed by the neutralization and dehydrobromination using pyridine, and finally crystallizing and purifying the product obtained with ethanol and charcoal.

With the new procedure it is possible to reduce the time of obtaining the final product, the reaction becomes endothermic instead of exothermic, which facilitates the work of the operators and allows for the scaling up of the reaction to superior levels.

The process significantly decreases the amount of chemicals in the reaction, some of them with toxic properties. Also the environmental negative impact from the process is diminished as the emission of the bromine vapors and other substances to the environment are eliminated and the residual liquids are cut in half.

5 Claims, No Drawings

METHOD FOR OBTAINING 2-BROMO-5-(2-BROMO-2-NITROVINYL)-FURAN

This application is a 371 of PCT/CU01/00001 filed on Jan. 18, 2000.

TECHNICAL SECTOR

The present invention relates to the Chemical branch, and in particular with a new process for obtaining 2-bromo-5-(2-bromo-2-nitrovinyl)-furan, a product of interest for human- and animal health due to its broad activity as microbicide.

PRIOR ART 2-bromo-5-(2-bromo-2-nitrovinyl)-furan was described for the first time in the international literature by authoress Z. N. Nazarova in 1972 (Z. N. Nazarova, 1972. "Synthesis of some furylnitroolefins with potential biological activity; Khim. Farm. Zh. 6(10,) pp. 5–8 and Z. N. Nazarova et al, 1972. "Physicochemical properties and reactivity of furylnitroolefins, Zh. Org. Khim. 8 (2), pp. 404–11).

Studies regarding the procedure for obtaining this product in a very pure form and with good yields, including its in vitro and in vivo actions, as well as pharmaceutical compositions containing said product, have been previously described (Canadian Patent No. 2,147,594).

DISCLOSURE OF THE INVENTION

The present invention is related to a novel procedure for obtaining 2-bromo-5-(2-bromo-2-nitrovinyl)-furan wherein the reaction is maintained by direct action of bromine to 2-nitrovinylfuran suspended in carbon disulfide. The novelty in this step is based on the addition of charcoal during the synthesis and the decreased quantity of solvent required. Normally, charcoal is used as a purifier due to its adsorptive properties. However, in the present invention charcoal acts as a catalyzer of the reaction. This is a new discovery. It is inventive and not obvious.

In a preferred embodiment of the process of this invention direct bromination of 2-nitrovinylfuran in a molar relation 1:2to 1:2.6 in carbon disulfide is carried out during periods of 1 to 3 hours, with temperature regulated in a range from 20 to 60° C., adding, from the beginning of the reaction, between 40 to 80% of charcoal in relation to the 2-nitrovinylfuran mass, followed of neutralization and dehydrobromination with pyridine at temperatures between 40 and 60° C., with subsequent purification of the product with ethanol and charcoal.

The addition of charcoal is advantageous because the reaction is no longer exothermic, which is evidenced in the constant temperature of the reactor and there is no emission of bromine through the condenser and the flask traps.

Neutralization and dehydrobromination of 2-bromo-5-(2-bromo-2-nitrovinyl)-furan contained in the reaction mixture is carried out with pyridine dissolved in carbon disulfide in very short time and without risks as the temperature is not increased to any great extend.

At the completion of this step, the product is filtered under heating and the solution is allowed to crystallize between −10 and −25° C. during 10–15 hours. This crude product has a higher purity (95%) than the obtained from the former technique (80%).

The crystals of crude product are purified by hot dissolution with ethanol and the addition of charcoal, finally the crystals obtained are recrystallized with ethanol.

In the reaction step gas absorption traps are connected to the reactor in order to absorb the hydrogen bromine that is liberated with the purpose of forming bromhydric acid. In this way, it does not escape to the environment and therefore it can be captured and marketed. Consequently, using the process of the present invention the volume of residuals is considerably reduced (by half) in comparison with known techniques. Furthermore, such residuals can be recovered with water traps and can be re-used due to their low level of contamination with bromide.

With this new process, the distillation step of the carbon disulfide excess, that always contained bromine, is eliminated. This decreases the process in general and the treatment of this aggressive residual is unnecessary.

After the purification process the product is the same as that obtained with the preceding technique, (Z)-2-bromo-5-(2-bromo-2-nitrovinyl)-furan; however the purity is grater than 99%.

EXAMPLES OF PERFORMANCE

Example 1

Five replicas of the method of the present invention were carried out using the scale of 2 moles. Table 1 represents the results obtained in said replicas.

TABLE 1

| Number of synthesis | Raw yield % | % Purity of crude product | % Purity of pure product | % Impurity |
|---|---|---|---|---|
| 1 | 52.91 | 95.26 | 99.26 | not detected |
| 2 | 74.70 | 99.33 | 99.45 | not detected |
| 3 | 53.45 | 96.77 | 99.57 | 0.05 |
| 4 | 77.39 | 96.67 | 99.05 | 0.3 |
| 5 | 65.76 | 95.75 | 99.05 | 0.6 |

Note: The crude purity percentage in the synthesis of the previous process described in the art is 80 and the volume of liquid residuals of the process is 0.7 liters, decreasing in a half in relation to the prior reported synthesis.

In summary the technical advantages of the present solution are:

It substantially diminishes the total time in the process of obtaining of 2-bromo-5-(2-bromo-2-nitrovinyl)-furan because the distillation step is eliminated and consequently the time in the neutralization step is notably decreased.

The amounts of solvent are reduced, which results in a reduction of production cost.

There is decrease in negative environmental impact, as free bromine is not escaping from the reactor and the residual liquids are cut in half.

By turning the reaction from exothermic to endothermic the work is carried out with more security and the process of scaling up the reaction to higher levels is facilitated The purity of the final product is superior.

What is claimed is:

1. Procedure for obtaining 2-bromo-5-(2-bromo-2-nitrovinyl)-furan wherein it is carried out the direct bromination of the 2-nitrovinylfuran using from the beginning of the reaction charcoal, followed by neutralization and dehydrobromination using pyridine dissolved in carbon disulfide, and finally crystallizing and purifying the product obtained with ethanol and charcoal.

2. Procedure according to claim 1 wherein for the direct bromination of the 2-nitrovinylfuran is carried out using a molar relation between 1:2 to 1:2.6 in carbon disulfide, during periods of 1 to 3 hours with regulation of temperature in a range of 20 to 60° C., using charcoal in a rate of 40–80% of charcoal regarding the mass of 2-nitrovinylfuran.

3. Procedure according to claim 1 wherein the neutralization and dehydrobromination reactions are carried out with pyridine dissolved in carbon disulfide at temperatures between 40 and 60° C.

4. Procedure according to claim 1 wherein the crystallization is carried out filtering under heating and allowing to crystallize the filtrate between −10 and −25° C. during 10 to 15 hours.

5. Procedure according to claim 1 wherein the purification is carried out by means of dissolution under heating with ethanol and addition of charcoal, and finally re-crystallizing the crystals this way obtained with ethanol and charcoal.

* * * * *